United States Patent
Fujiwara et al.

(10) Patent No.: US 10,161,935 B2
(45) Date of Patent: Dec. 25, 2018

(54) TEST SUBSTANCE MEASUREMENT KIT AND TEST SUBSTANCE MEASUREMENT METHOD

(71) Applicant: FUJIFILM Corporation, Tokyo (JP)

(72) Inventors: Nobuhiko Fujiwara, Ashigarakami-gun (JP); Noriyuki Kasagi, Ashigarakami-gun (JP); Toshihito Kimura, Ashigarakami-gun (JP); Kazuhiro Nakamura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 523 days.

(21) Appl. No.: 14/730,378

(22) Filed: Jun. 4, 2015

(65) Prior Publication Data

US 2015/0355175 A1    Dec. 10, 2015

(30) Foreign Application Priority Data

Jun. 5, 2014  (JP) ................................. 2014-116764

(51) Int. Cl.
| | |
|---|---|
| *G01N 21/64* | (2006.01) |
| *G01N 21/82* | (2006.01) |
| *G01N 21/552* | (2014.01) |
| *G01N 33/543* | (2006.01) |
| *G01N 33/553* | (2006.01) |

(52) U.S. Cl.
CPC ..... *G01N 33/54386* (2013.01); *G01N 21/553* (2013.01); *G01N 21/64* (2013.01); *G01N 21/648* (2013.01); *G01N 21/82* (2013.01); *G01N 33/54373* (2013.01); *G01N 33/553* (2013.01); *G01N 2021/825* (2013.01)

(58) Field of Classification Search
None
See application file for complete search history.

(56) References Cited

U.S. PATENT DOCUMENTS

| | | | |
|---|---|---|---|
| 4,680,274 A | | 7/1987 | Sakai et al. |
| 5,096,837 A | * | 3/1992 | Fan .................. G01N 33/54313 435/7.1 |
| 5,447,837 A | * | 9/1995 | Urnovitz .......... G01N 33/54386 435/5 |
| 2007/0059761 A1 | * | 3/2007 | Bambad ................ B82Y 15/00 435/7.1 |
| 2009/0079978 A1 | | 3/2009 | Kimura |
| 2009/0261269 A1 | * | 10/2009 | Horii ..................... B82Y 15/00 250/459.1 |
| 2013/0078738 A1 | | 3/2013 | Watanabe et al. |

FOREIGN PATENT DOCUMENTS

| | | | | |
|---|---|---|---|---|
| JP | 60-256057 A | 12/1985 | | |
| JP | 11-337551 A | 12/1999 | | |
| JP | 2000-221196 A | 8/2000 | | |
| JP | 2003-057173 A | * | 2/2003 | ........... G01N 21/553 |
| JP | 2003-57173 A | 2/2003 | | |
| JP | 2007-127438 A | 5/2007 | | |
| JP | 2009-79970 A | 4/2009 | | |
| JP | 2010-19553 A | 1/2010 | | |
| JP | 2013-83632 A | 5/2013 | | |

OTHER PUBLICATIONS

Extended European Search Report, dated Oct. 14, 2015, for European Application No. 15169904.8.

* cited by examiner

*Primary Examiner* — Lisa V Cook (74) *Attorney, Agent, or Firm* — Birch, Stewart, Kolasch & Birch, LLP (57) ABSTRACT

To provide a test substance measurement method and a test substance measurement kit adapted to improve the accuracy of the measurement of a test substance. A test substance measurement kit includes: fluorescent particles which are modified with a first binding substance having specific bindability to a test substance; non-fluorescent particles which are modified with a second binding substance having no specific bindability to the test substance; and a substrate on which a first metal film to which a third binding substance having specific bindability to the test substance is fixed, and a second metal film to which a fourth binding substance having no bindability to the test substance, but having bindability to the first binding substance is fixed, and which has a smaller thickness than the first metal film are formed.

14 Claims, 6 Drawing Sheets

TEST SUBSTANCE MEASUREMENT KIT AND TEST SUBSTANCE MEASUREMENT METHOD

CROSS REFERENCE TO RELATED APPLICATIONS

The present application claims priority under 35 U.S.C. § 119 to Japanese Patent Application No. 2014-116764, filed on Jun. 5, 2014, all of which are hereby expressly incorporated by reference into the present application.

BACKGROUND OF THE INVENTION

1. Field of the Invention

The present invention relates to a test substance measurement kit and a test substance measurement method for measuring a test substance based on an antigen-antibody reaction using an insoluble carrier.

2. Description of the Related Art

A fluorescence detection method is widely used as a high-sensitive and easy measurement method for determining the amounts of protein, enzymes, inorganic compounds and the like contained in a test substance. The fluorescence detection method is a method of confirming the presence of a test substance by detecting the fluorescence produced when a test sample considered to contain the test substance, which emits the fluorescence by being excited by light having a specific wavelength, is irradiated with excitation light having the specific wavelength. When the test substance is not a fluorescent material, a method of confirming the presence of a test substance by bringing a substance, which is labeled with a fluorescent dye and specifically binds to the test substance, into contact with a test sample and by then detecting the fluorescence in the same manner as described above is also widely used.

In such a fluorescence detection method, a method using the effect of electric field enhancement by plasmon resonance to improve detection sensitivity has been known. In this method, a sensor chip provided with a metal film in a predetermined region on a transparent support is provided in order to generate plasmon resonance. Excitation light is made to incident at an angle equal to or larger than a total reflection angle from a surface of the support opposite a surface on which the metal film is formed to an interface between the support and the metal film. Due to the irradiation with the excitation light, surface plasmon is generated on the metal film, the intensity of fluorescence is increased due to an electric field enhancement action occurring by the generation of the surface plasmon, and a signal-to-noise ratio (S/N ratio) is improved. In the fluorescence detection method with the surface plasmon excitation (hereinafter, referred to as "SPF method"), an increase in signal intensity by approximately ten times is obtained compared to a fluorescence detection method with vertical illumination excitation, and thus the measurement can be performed with high sensitivity.

As an example of the SPF method, an example using a dielectric plate having a measurement region and a reference measurement region formed thereon is described in Patent Document 1. The measurement region and the reference measurement region are constituted by metal films having different thicknesses. A substance which specifically binds to a test substance is fixed to the metal film in the measurement region, and no substance is fixed to the metal film in the reference measurement region.

An immunodiagnosis system using a conventional SPF method employs a method of increasing measurement accuracy by correcting a signal value of a measurement region which reacts with a test substance with a signal value of a correction region proportional to the amount of a test sample in order to reduce errors in the measurement and a variation in the amount of a reagent contained in the product.

For example, Patent Document 2 discloses a technique including: preparing a solution in which fluorescent particles in which a first binding substance which can bind to a test substance and a third binding substance which can bind to a second binding substance having bindability to the first binding substance and does not bind to the test substance are bound to each other are mixed in a test sample; and pouring the solution into a channel in which a measurement region to which a fourth binding substance which does not bind to the first binding substance and the third binding substance, but binds to the test substance is fixed, and a correction region to which the second binding substance is fixed are formed to correct a signal detected in the measurement region using a signal detected in the correction region, thereby reducing a difference in temperature dependency between a signal value of the correction region and a signal value of the measurement region.

Patent Document 3 discloses an example in which in an analysis device in which in a sensor chip using surface plasmon resonance, an error in a detection signal due to the inclination of the sensor chip is corrected to make an accurate concentration distribution, metal films constituting a correction region and a measurement region have different thicknesses. Specifically, a sensor chip in which the metal film in the correction region has a smaller thickness than that in the measurement region and a substance which binds to a test substance is fixed only to the measurement region is used.

As a phenomenon caused by a test sample, a problem in which a positive test sample which also reacts with a negative test sample containing no test substance exists and a false positive is shown has been conventionally recognized.

Patent Document 4 describes a technique of reducing a false positive using ultrafine particles having a size of 0.2 μm or less in order to prevent a non-specific immune reaction of sensitizing particles having a size of 0.3 μm to 2.0 μm in an immunological measurement method, particularly, in an immunological measurement method using aggregation.

Patent Document 5 describes a method of detecting a test substance through an immunoagglutination reaction using sensitizing particles having a size of 0.4 μm) or greater, in which insoluble carrier particles having a size of 0.01 μm to 0.5 μm are used as particles to be used in blocking.

Patent Document 6 describes a method of adding, to particles which are smaller than particles which react specifically, a material to which an antibody or antigen which does not immunologically react with a test substance is fixed, in order to suppress a non-specific reaction.

Patent Document 7 describes a non-specific reaction inhibitor which is used in immunoassay using immunoassay particles in which an antibody or antigen immunologically reacting with a test substance is supported on a carrier having an average particle diameter of 0.05 μm to 0.5 μm, and which includes an insoluble carrier supporting an antibody or antigen which does not immunologically react with the test substance in the presence of an organic solvent, in which the average particle diameter of the insoluble carrier is smaller than that of the carrier.

Patent Document 8 describes a detection method of distinguishing between a specific binding reaction and a non-specific binding reaction between various biomolecules, in which the influence of the non-specific reaction is suppressed with particles having an outer diameter of 1 μm or less.

CITATION LIST

Patent Documents

[Patent Document 1] JP2009-079970A
[Patent Document 2] JP2013-083632A
[Patent Document 3] JP2003-057173A
[Patent Document 4] JP1985-256057A (JP-S60-256057A)
[Patent Document 5] JP2000-221196A
[Patent Document 6] JP1999-337551A (JP-H11-337551A)
[Patent Document 7] JP2007-127438A
[Patent Document 8] JP2010-19553A

SUMMARY OF THE INVENTION

Techniques of reducing problems of a false positive using a large number of fine particles have been known as above. However, since these techniques use a large number of fine particles, in a system having a possibility of adhesion of fine particles to each of the measurement region and the correction region as described in Patent Document 2, a large difference is generated between the measurement region and the correction region in terms of the number of fine particles adhered thereto. As a result, the refractive index is significantly changed in the measurement region and in the correction region, and thus a change in the degree of plasmon enhancement with a deviation of an incidence angle of excitation light from a design value is very different between the correction region and the measurement region, and thus the accuracy of the correction using a signal value of the correction region may be reduced. In Patent Document 2, there is no recognition of such a problem.

In the techniques described in Patent Documents 1 and 3, particles do not adhere to a plurality of regions which are light detection targets, and thus there is no recognition of a problem in which the correction accuracy is reduced due to the difference in the number of adhering particles.

The invention is contrived in view of the circumstances and an object thereof is to provide a test substance measurement kit and a test substance measurement method adapted to improve the accuracy of the measurement of a test substance.

A test substance measurement kit according to the invention includes: first dry particles which have a label and are modified with a first binding substance having specific bindability to a test substance; second dry particles which are modified with a second binding substance having no specific bindability to the test substance; and a substrate on which a first metal film to which a third binding substance having specific bindability to the test substance or a substance having bindability to the first binding substance is fixed, and a second metal film to which a fourth binding substance having no bindability to the test substance, but having bindability to the first binding substance is fixed, and which has a smaller thickness than the first metal film are formed.

A test substance measurement method according to the invention includes: bringing a solution containing a test substance, first dry particles which have a label and are modified with a first binding substance having specific bindability to the test substance, and second dry particles which are modified with a second binding substance having no specific bindability to the test substance into contact with a first metal film to which a third binding substance having specific bindability to the test substance or a substance having bindability to the first binding substance is fixed, and a second metal film to which a fourth binding substance having no bindability to the test substance, but having bindability to the first binding substance is fixed and which has a smaller thickness than the first metal film; detecting a signal according to the label from each of the first metal film and the second metal film; and correcting the signal detected from the first metal film using the signal detected from the second metal film.

According to the invention, it is possible to provide a test substance measurement kit and a test substance measurement method adapted to improve the accuracy of the measurement of a test substance.

DESCRIPTION OF THE PREFERRED EMBODIMENTS

Hereinafter, embodiments of the invention will be described with reference to the drawings.

Figure 1:
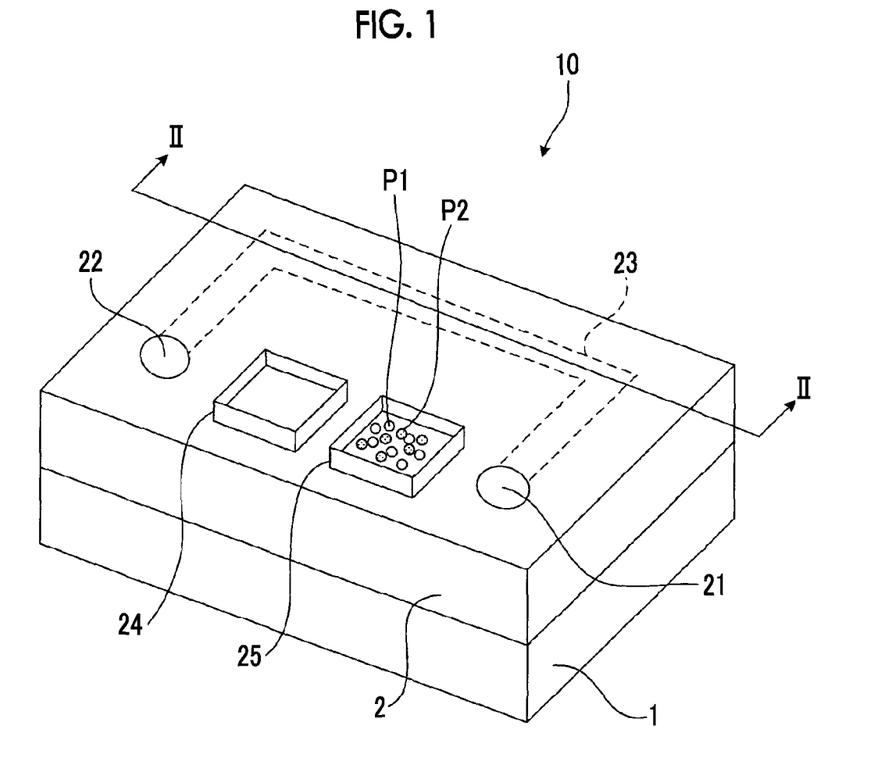
FIG. 1 is a diagram showing a schematic configuration of a test substance measurement kit 10 according to an embodiment of the invention.
Figure 2:
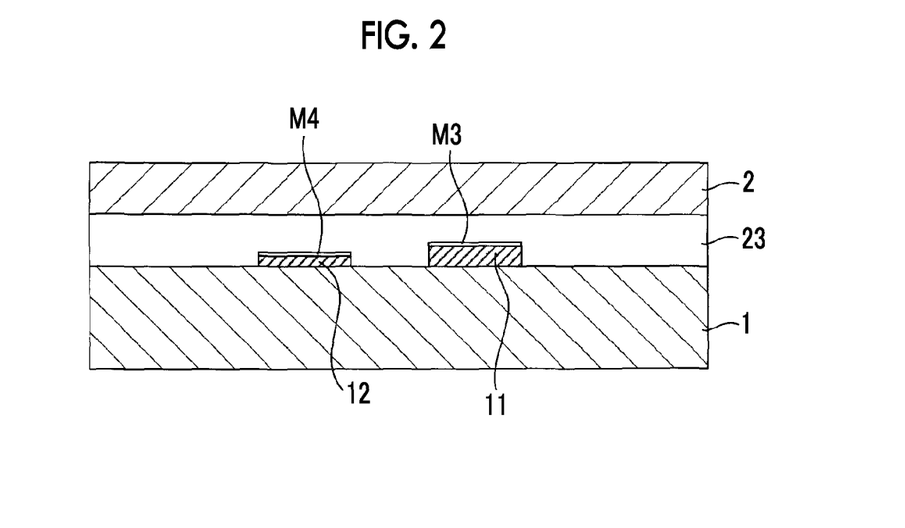
FIG. 2 is a schematic cross-sectional view taken along line II-II shown in FIG. 1.

FIG. 1 is a diagram showing a schematic configuration of a test substance measurement kit 10 according to an embodiment of the invention. The test substance measurement kit 10 is used to detect a specific test substance contained in a test sample such as blood or the like of a human or an animal. FIG. 2 is a schematic cross-sectional view taken along line II-II shown in FIG. 1.

The test substance measurement kit 10 is configured to mainly include a substrate 1 and a channel forming member 2.

In the example of FIG. 1, the channel forming member 2 has a concave portion 23 having a whole bridge shape formed on one surface thereof. The foregoing one surface of the channel forming member 2 is stuck to a surface of the substrate 1. As shown in FIG. 2, a space surrounded by an inner wall of the concave portion 23 and the substrate 1 forms a channel for allowing a solution containing a test sample to flow.

The channel forming member 2 has an inflow port 21 and a discharge port 22 formed to penetrate from one surface to the other surface. The inflow port 21 is formed to pour the solution containing the test sample into the channel formed of the space surrounded by the inner wall of the concave portion 23 and the substrate 1. The discharge port 22 is formed to discharge the solution containing the test sample from the channel to the outside.

A container 24 which stores a substance useful in the invention, e.g., a substance (not shown) useful in prevention of the aggregation of dry particles, and a container 25 which stores first dry particles P1, having a label and modified by a first binding substance M1 having specific bindability to a test substance which is a measurement target of the test substance measurement kit 10, and second dry particles P2, having no label and modified by a second binding substance M2 having no specific bindability to the test substance, are fixed to the other surface of the channel forming member 2. Examples of the substance stored in the container 24 include magnesium chloride.

The type of the label of the first dry particles P1 is not particularly limited as long as the label can be detected through the SPF method. The label is preferably a fluorescent substance.

As shown in FIG. 2, a first metal film 11 and a second metal film 12 are formed on the substrate 1. Specifically, in a part in which the channel is formed on the surface of the substrate 1, the first metal film 11 and the second metal film 12 are arranged and formed in this order along the channel from the side of the inflow port 21. In this specification, the expression "formed on the substrate" includes a case in which the metal film is not directly brought into contact with the substrate, but formed via another layer, in addition to a case in which the metal film is disposed to be directly brought into contact with the surface of the substrate. A substance on which surface plasmon resonance can be generated can be used as the metal constituting the first metal film 11 and the second metal film 12. In order to effectively induce the plasmon resonance, a material containing gold is preferably used as the material of the first metal film 11 and the second metal film 12, and gold is more preferably used to constitute the whole metal film.

A third binding substance M3 having specific bindability to the test substance is fixed to a surface of the first metal film 11. The first metal film 11 constitutes a measurement region for measuring the amount of the test substance.

A fourth binding substance M4 having no bindability to the test substance, but having bindability to each of the first binding substance M1 and the second binding substance M2 is fixed to a surface of the second metal film 12. The second metal film 12 has a smaller thickness than the first metal film 11. The second metal film 12 constitutes a correction region for correcting a signal measured in the measurement region.

Figure 3:
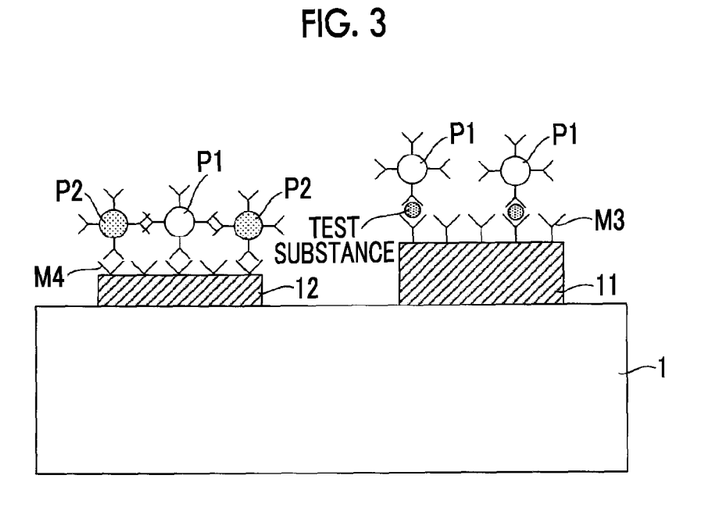
FIG. 3 is a diagram illustrating an action in the vicinity of a metal film of the test substance measurement kit 10.

FIG. 3 is a diagram for illustrating a substance captured by the first metal film 11 and the second metal film 12 when the test substance measurement kit 10 is used. FIG. 3 shows a state when a measurement method based on a sandwich method is employed.

When the test substance measurement kit 10 is used, a solution in which a test sample (or extract thereof) which may contain a test substance, a substance stored in the container 24, first dry particles P1, and second dry particles P2 are mixed with each other is prepared. When the test substance exists in the test sample, the first binding substance M1 modifying the first dry particles P1 and the test substance bind to each other in the solution. This solution is poured from the inflow port 21 and moved in the channel by sucking the air in the channel from the discharge port 22 so that the solution is brought into contact with the first metal film 11 and the second metal film 12 in order.

When the test substance exists in the test sample, the third binding substance M3 on the first metal film 11 binds to the test substance binding to the first dry particles P1, and the first dry particles P1 according to the amount of the test substance are fixed to the first metal film 11 as shown in FIG. 3.

On the second metal film 12, the fourth binding substance M4 on the second metal film 12 binds to the first dry particles P1 and the second dry particles P2 which are not fixed to, but pass the first metal film 11, and the first dry particles P1 and the second dry particles P2 are fixed.

The proportion of the test substance in the solution is very small. Accordingly, according to the test substance measurement kit 10, the number of the dry particles fixed to the second metal film 12 is far larger than the number of the dry particles fixed to the first metal film 11.

Figure 4:
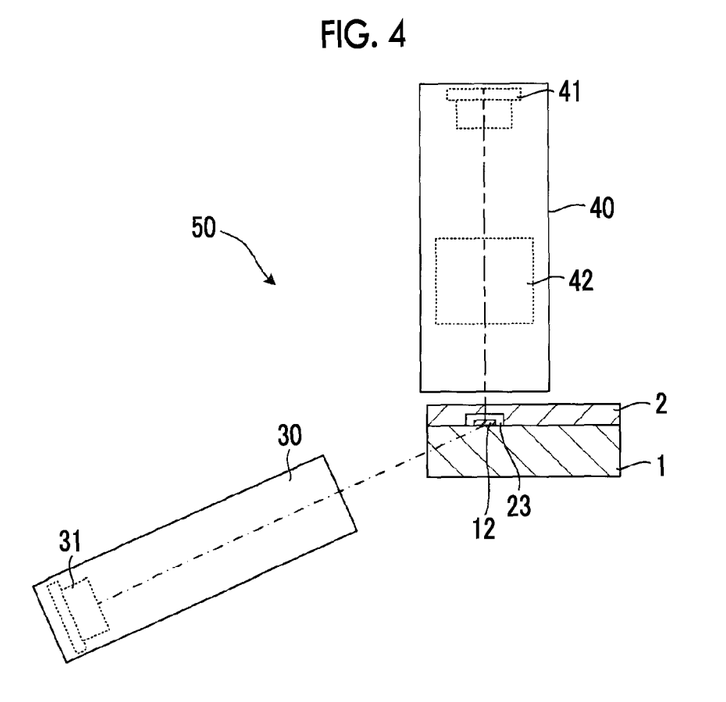
FIG. 4 is a diagram showing a schematic configuration of a test substance measurement device which measures a test substance using the test substance measurement kit 10.

FIG. 4 is a diagram showing a schematic configuration of a test substance measurement device 50.

The test substance measurement device 50 has: a lighting portion 30 which has a built-in light source 31 for applying excitation light and applies the excitation light applied from the light source 31 from the rear surface side of the substrate 1 to an interface between the substrate 1 and the first and second metal films 11 and 12 at a predetermined angle; and a measurement portion 40 for detecting the fluorescence produced from the surfaces of the first metal film 11 and the second metal film 12 with the incidence of the excitation light. The measurement portion 40 includes a light quantity detecting portion 41 such as a photodiode, and an excitation light cut filter 42 which cuts the light applied from the light source 31 is provided before the light quantity detecting portion 41 so that the light quantity detecting portion 41 does not detect the light applied from the lighting portion 30.

The test substance measurement device 50 further has an arithmetic processing portion (not shown). The arithmetic processing portion measures the amount of the test substance based on a signal according to the light quantity detected by the light quantity detecting portion 41. Specifically, the amount of the test substance is measured with high accuracy by correcting information (signal) according to the light (fluorescence from the fluorescent substance of the first dry particles P1 of FIG. 3) emitted from the first metal film 11 with information (signal) according to the light (fluorescence from the fluorescent substance of the first dry particles P1 of FIG. 3) emitted from the second metal film 12.

Examples of this correction method include dividing the measurement information value in the measurement region by the measurement information value in the correction region, but the correction method is not limited thereto. For example, a conversion factor corresponding to the measurement information value in the correction region may be calculated from a relational expression to correct the measurement information value in the measurement region, or the measurement information value in the correction region may be subtracted from the measurement information value in the measurement region to perform the correction.

In the test substance measurement device 50, it is necessary to determine the incidence angle of the excitation light to be applied to the interface between the substrate 1 and the first and second metal films 11 and 12 from the lighting portion 30 with high accuracy. However, in the actual device, this incidence angle may deviate from a design value due to an assembling error, a production error, and the like.

Figure 5:
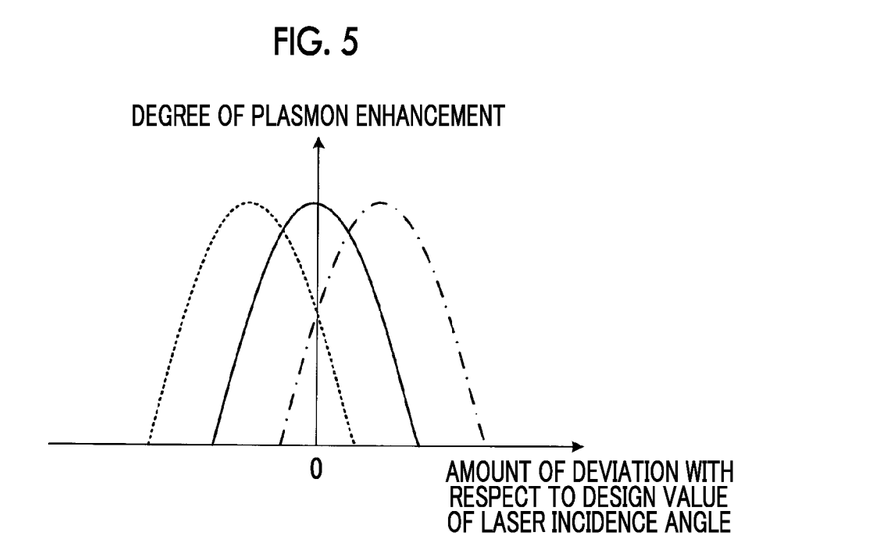
FIG. 5 is a diagram for illustrating the relationship between a variation in the incidence angle of excitation light and the degree of plasmon enhancement.

FIG. 5 is a diagram showing the result of an examination of a change in the degree of plasmon enhancement when the incidence angle of the excitation light deviates from the design value. The horizontal axis in FIG. 5 indicates the amount of deviation of the incidence angle of the excitation light from the design value.

FIG. 5 shows three waveforms. The waveform expressed by the solid line indicates a change in the degree of plasmon enhancement when the thickness of the metal film irradiated with the excitation light is set as a first value and the number of dry particles captured on this metal film is set as a second value.

The waveform expressed by the dashed line indicates a change in the plasmon enhancement when the thickness of the metal film irradiated with the excitation light is smaller than the first value and the number of dry particles captured on this metal film is smaller than the second value.

The waveform expressed by the broken line indicates a change in the plasmon enhancement when the thickness of the metal film irradiated with the excitation light is larger than the first value and the number of dry particles captured on this metal film is larger than the second value.

As shown in FIG. 5, it is found that the characteristic waveform of the degree of plasmon enhancement is changed with the thickness of the metal film and the number of adhering particles.

As described above, according to the test substance measurement kit 10, the number of the dry particles adhering to the second metal film 12 is far larger than the number of the dry particles adhering to the first metal film 11. Therefore, on the assumption that the first metal film 11 and the second metal film 12 have the same thickness, when the characteristics of the degree of plasmon enhancement in the first metal film 11 are as shown by the solid-line waveform of FIG. 5, the characteristics of the degree of plasmon enhancement in the second metal film 12 are shifted to the left side from the solid-line waveform of FIG. 5, and the correction using the information of the correction region cannot be accurately performed.

Therefore, in the test substance measurement kit 10, a reduction in correction accuracy due to the difference in the number of adhering particles is prevented by making the film thickness of the second metal film 12 constituting the correction region smaller than the film thickness of the first metal film 11 constituting the measurement region. That is, the film thicknesses of the first metal film 11 and the second metal film 12 are determined so that the waveform indicating the change in the degree of plasmon enhancement shown in FIG. 5 in the correction region almost matches that in the measurement region. Accordingly, even when the incidence angle of the excitation light deviates from the design value, the test substance can be detected with high accuracy without a large difference in the degree of plasmon enhancement between the correction region and the measurement region.

The film thicknesses of the first metal film 11 and the second metal film 12 are not particularly limited as long as the surface plasmon phenomenon can be sufficiently detected. The first metal film 11 preferably has an average film thickness of 35 nm to 42 nm and the second metal film 12 preferably has an average film thickness of 24 nm to 32 nm since a reduction in correction accuracy due to a fluctuation in the incidence angle of the excitation light and a fluctuation in the film thickness of the metal film is prevented.

Although the difference between the average film thickness of the first metal film 11 and the average film thickness of the second metal film 12 depends on the number of particles adhering to the second metal film 12, it is preferably 10% or greater of the average film thickness of the first metal film 11. The average film thicknesses of the first metal film 11 and the second metal film 12 are preferably 500 nm or less since the surface plasmon phenomenon in the medium cannot be sufficiently detected when the average film thicknesses are greater than 500 nm. The average film thickness of the metal film can be measured using a spectroscopic ellipsometer. In addition, based on values measured using the spectroscopic ellipsometer, a correspondence table between the values and transmissivities obtained using a spectrophotometer may be prepared to obtain the average film thickness by conversion from the transmissivity of the spectrophotometer. As another method, a method of measuring a film thickness by observing a segment of the substrate on which the preparation of the metal film has been completed using an electron microscope can also be used.

Hereinafter, constituent elements of the test substance measurement kit 10 will be described in detail.

Test Substance

The type of the test substance which is a detection target of the test substance measurement kit 10 is not particularly limited, and examples thereof include cortisol, insulin-like growth factor 1 (IGF-I), insulin-like growth factor-binding protein-3, (IGFBP-3), luteinizing hormone (LH), thyroid-stimulating hormone (TSH), antidiuretic hormone (ADH), growth hormone (GH), urinary GH, adrenocorticotropic hormone (ACTH), prolactin, follicle-stimulating hormone (FSH), thyroxine-binding globulin (TBG), TSH-stimulating receptor antibodies (TSAb), thyroxine (T4), anti-thyroid peroxidase antibodies (anti-TPO antibodies), microsome antibodies, anti-thyroglobulin antibodies, thyroglobulin, triiodothyronine (T3), fT4, fT3, 1,25-(OH)2 vitamin D, type I collagen crosslinked N-telopeptide (NTx), intact type I procollagen-N-propeptide (Intact PINP), osteocalcin, calcitonin, bone-specific alkaline phosphatase (BAP), deoxypyridinoline, parathyroid hormone (PTH), parathyroid hormone-related protein (PTHrP), 5-hydroxyindoleacetic acid (5-HIAA), homovanillic acid (HVA), L-dopa, 3-methoxy-4-hydroxyphenyl ethylene glycol (MHPG), vanillylmandelic acid (VMA), catecholamine, serotonin, metanephrine, 11-deoxycortisol, 17-ketogenic steroid (17-KGS), 17-OH-pregnenolone, aldosterone, androsterone, androstenedione, 11-hydroxycorticosteroid (11-OHCS), corticosterone, cortisone, deoxycorticosterone (DOC), dehydroepiandrosterone sulfate (DHEA-S), pregnenolone, 5α dihydrotestosterone, human chorionic gonadotropin (HCG) β subunit, estradiol (E2), estriol (E3), estrogen, estrone (E1), human chorionic gonadotropin (HCG), testosterone, pregnanediol, pregnanetriol, progesterone, C peptide (CPR), vasoactive intestinal peptide (VIP), insulin, gastrin, glucagon, anti-glutamic acid decarboxylase antibodies (anti-GAD antibodies), anti-insulinoma-associated antigen-2 antibodies (anti-IA-2 antibodies), anti-insulin antibodies, cardiac troponin T, ventricular myosin light chain I, human heart-derived fatty acid-binding protein (H-FABP), human atrial natriuretic peptide (HANP), brain natriuretic peptide (BNP), n-terminal fragment of brain natriuretic peptide (NT-proBNP), and myoglobin. A particularly preferable example of the test substance is TSH.

Substrate

Any material may be used as the substrate 1 as long as it can be used in the SPF method. For example, optical glass such as borosilicate glass (BK7), which is a type of general optical glass, or a synthetic resin such as polymethyl meth-acrylate, polyethylene terephthalate, polycarbonate, or a cycloolefin polymer which is a material transparent to laser beams can be used. The substrate is preferably made of a material which does not exhibit anisotropy to polarized light and has excellent processability.

Metal Film

Preferable examples of the metal constituting the first metal film 11 and the second metal film 12 include free-electron metals such as gold, silver, copper, aluminum, and platinum. These metals can be used alone or in combination.

Figure 6:
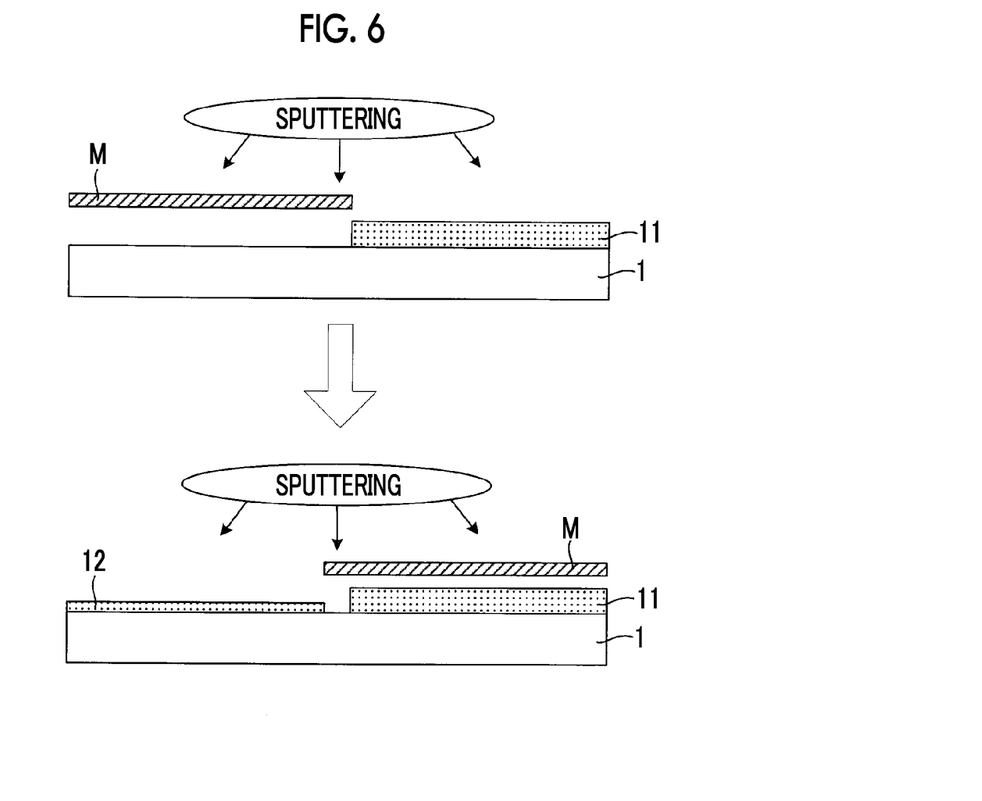
FIG. 6 is a diagram showing an example of a method of forming metal films having different thicknesses.

In the preparation of the metal films constituting the measurement region and the correction region, the method of separately controlling the film thickness in the correction region and in the measurement region when the metal films are formed on the substrate by sputtering or the like is not particularly limited. As shown in FIG. 6, a method of controlling a film thickness including: preparing a mask M with which a film can be formed in each of the regions; and performing film formation plural times on the substrate 1 to obtain a predetermined film thickness using each mask M can be employed.

The metal film may be formed using a conventional method such as a sputtering method, a vapor deposition method, an ion plating method, an electroplating method, or an electroless plating method. The metal film is preferably formed using a sputtering method to realize good close contact with the substrate on which the metal film is prepared. An intermediate layer made of chromium or the like may be provided between the substrate and the metal film in consideration of the adhesiveness to the substrate on which the metal film is formed. When the intermediate layer made of chromium or the like is provided, the thickness of the intermediate layer is preferably 0.1 nm to 10 nm.

Third Binding Substance M3

The third binding substance M3 is not particularly limited as long as it can capture the test substance. Preferable examples thereof include antigens, antibodies, and complexes thereof, and antibodies are preferably used. When the third binding substance M3 is an antibody, for example, antiserum prepared from the serum of an animal immunized with the test substance, an immunoglobulin fraction purified from antiserum, a monoclonal antibody obtained by cell fusion using splenocytes of an animal immunized with the test substance or fragments thereof (for example, F(ab')2, Fab, Fab', or Fv), and the like can be used as an antibody having specificity for the test substance. These antibodies can be prepared using conventional methods. Moreover, these antibodies may be modified antibodies such as chimeric antibodies, and it is also possible to use both commercially available antibodies and antibodies prepared from animal serum or culture supernatant using known methods.

The antibodies can be used regardless of the type of animal, the subclass thereof, and the like. For example, the antibodies which can be used in the invention include antibodies derived from living organisms such as mice, rats, hamsters, goats, rabbits, sheep, cows, or chickens in which an immune reaction may occur. Specific examples thereof include mouse IgG mouse IgM, rat IgG rat IgM, hamster IgQ hamster IgM, rabbit IgG; rabbit IgM, goat IgG; goat IgM, sheep IgG; sheep IgM, cow IgG cow IgM, and chicken IgY, and both polyclonal and monoclonal antibodies can be used. Fragmented antibodies are molecules which have at least one antigen-binding site and are derived from complete antibodies, and specific examples thereof include Fab and F(ab')2. These fragmented antibodies are molecules obtained through an enzymatic or chemical process or using a genetic engineering method.

The method of immobilizing a binding substance such as an antibody or an antigen onto particles is described in, for example, JP2000-206115A, the protocol attached to Fluo-Spheres (registered trade mark) polystyrene microspheres F8813 (Molecular Probes), and the like, and any of known methods of preparing a reagent for an immunoagglutination reaction can be used. As the principle of immobilizing an antibody as a binding substance onto particles, any of principles of physical adsorption and chemical binding established by covalent bonds can be employed. As a blocking agent covering the particle surface which has not been covered with the antibody after the immobilization of the antibody onto the particles, known substances, e.g., bovine serum albumin (BSA), skim milk, casein, soybean-derived components, fish-derived components, polyethylene glycol, and commercially available blocking agents for an immune reaction containing the above substances or substances having the same properties as those of the above substances can be used. If necessary, these blocking agents can be subjected to a pretreatment such as partial denaturation by means of heat, an acid, an alkali, and the like.

Fourth Binding Substance M4

As the fourth binding substance M4, for example, antibodies against the binding substance (antibody) and compounds having affinity for the first binding substance M1 and the second binding substance M2, such as proteins (Protein A and Protein G) binding to the binding substance (antibody), can be preferably used. Among these, antibodies can be preferably used. In addition, compounds in which a part of the first binding substance M1 binding to the first dry particles P1 having a label has a ligand-nonligand relationship with the fourth binding substance M4 can be preferably used. The method of immobilizing the fourth binding substance M4 such as an antibody onto the substrate is described in, for example, Tech Notes Vol. 2 to 12 provided by Nunc, and the like, and any of known methods of preparing general ELISA reagents may be used. In addition, surface modification by placing a self-assembled monolayer (SAM) or the like on the substrate may also be performed, and as the principle of immobilizing an antibody as the fourth binding substance M4 onto the substrate, any of principles of physical adsorption and chemical binding established by covalent bonds can be employed. As a blocking agent covering the substrate surface which has not been covered with the antibody after the immobilization of the antibody onto the substrate, known substances, e.g., bovine serum albumin (BSA), skim milk, casein, soybean-derived components, fish-derived components, polyethylene glycol, and commercially available blocking agents for an immune reaction containing the above substances or substances having the same properties as those of the above substances can be used. If necessary, these blocking agents can be subjected to a pretreatment such as partial denaturation by means of heat, an acid, an alkali, and the like.

Dry Particles

The first dry particles P1 and the second dry particles P2 are stored in the containers 24 and 25, respectively, in a dry state, and mixed with a solution containing a test substance in the measurement, and thus used in a state of being dispersed in the solution. When these particles are stored in the container 25 in a solution state without being dried, the particles may aggregate or fuse together, and thus have a large size, and the measurement accuracy may be changed. Accordingly, the first dry particles P1 and the second dry particles P2 are stored in a dry state. Here, the dry state is a state in which the ratio of the moisture to the dry weight is 30% or less, and the ratio is preferably 20% or less, and more preferably 15% or less. In order to maintain good measurement reproducibility, the average particle diameter of the first dry particles P1 and the second dry particles P2 is preferably 100 nm to 200 nm. When the average particle diameter of the particles is 200 nm or less, good dispersibility can be realized when the particles are mixed with the solution containing the test substance, the immune reaction thought to be caused by a non-specific adsorbate can be suppressed, and reproducibility of ability to prevent a false positive can be maintained. When the average particle diameter of the particles is 100 nm or greater, good signal sensitivity can be realized. The average particle diameter of the first dry particles P1 and the second dry particles P2 is more preferably 100 nm to 190 nm, and even more preferably 130 nm to 180 nm.

Regarding the use ratio of the first dry particles P1 and the second dry particles P2, the mass ratio of the second dry particles P2 to the first dry particles P1 is preferably 1 to 6, and more preferably 2 to 6. Therefore, the ability to prevent a false positive can be increased.

Average Particle Diameter Measurement Method

The average particle diameter of the first dry particles P1 and the second dry particles P2 can be measured using a commercially available particle size analyzer or the like. As a particle size distribution measurement method, optical microscopy, confocal laser microscopy, electron microscopy, atomic force microscopy, a static light scattering method, a laser diffraction method, a dynamic light scattering method, a centrifugal sedimentation method, an electrical pulse measurement method, a chromatography method, an ultrasonic attenuation method, and the like are known, and devices corresponding to the principles are commercially available.

In the invention, a dynamic light scattering method can be preferably used from the viewpoints of the range of particle size and the easy measurement. Examples of a commercially available measurement device using dynamic light scattering include Nanotrack UPA (Nikkiso Co., Ltd.), a dynamic light scattering-type particle size distribution measurement device LB-550 (Horiba, Ltd.), and a concentration-system particle size analyzer FPAR-1000 (Otsuka Electronics Co., Ltd.) In the invention, a value of the median diameter (d=50) measured at a measurement temperature of 25° C. can be obtained as the average particle diameter.

Material of Dry Particles

The material of the first dry particles P1 and the second dry particles P2 is not particularly limited and latex particles are preferably used. Specific examples of the material of latex include polystyrene, styrene-acrylic acid copolymers, styrene-methacrylic acid copolymers, styrene-glycidyl (meth)acrylate copolymers, styrene-styrenesulfonate copolymers, methacrylic acid polymers, acrylic acid polymers, acrylonitrile-butadiene-styrene copolymers, vinyl chloride-acrylic acid ester copolymers, and polyvinyl acetate acrylate. As the latex, copolymers containing at least styrene as a monomer are preferable, and copolymers of styrene and acrylic acid or methacrylic acid are particularly preferable.

The latex preparation method is not particularly limited and the latex can be prepared using an arbitrary polymerization method. Since it becomes difficult to conduct antibody immobilization when the antibody labeling is performed in the presence of a surfactant, soap-free polymerization is preferable in the preparation of the latex.

The latex particles according to a particularly preferable embodiment contain styrene and acrylic acid or methacrylic acid, and are produced by performing polymerization by means of adding dropwise a polymerization initiator to an aqueous suspension having a styrene concentration of 1.4 M or lower. It is not preferable to use an aqueous suspension having a styrene concentration of higher than 1.4 M since the latex particles generated in the polymerization system bind to each other and the average particle diameter of the generated latex particles is thus increased. The temperature of the aqueous suspension is preferably increased to 75° C. to 100° C. before the polymerization initiator is added. It is preferable to increase the temperature as described above since the initiator can be decomposed simultaneously with the addition of the initiator and radicals can be generated in an instant in the polymerization system, and consumption of monomers can be started, whereby the effect of making the diameter of the latex particles uniform is obtained.

The polymerization initiator is not particularly limited as long as it can initiate polymerization, and known polymerization initiators can be used. For example, potassium persulfate (KPS), 2,2'-azobisisobutyronitrile, 2,2'-azobis(2,4-dimethyl)valeronitrile, 2,2'-azobis(4-methoxy-2,4-dimethylvaleronitrile), benzoyl peroxide, 2,4-dichloroperoxide, isopropyl peroxycarbonate, cumene hydroperoxide, lauroyl peroxide and the like can be used for polymerization. Potassium persulfate is particularly preferably used to perform the polymerization. The amount of the polymerization initiator used is preferably approximately 0.1% by mass to 5% by mass of the monomer composition.

The polymerization can also be performed in the presence of a crosslinking agent. As the crosslinking agent, for example, divinyl benzene or 1,4-butadiene can be used, but the crosslinking agent is not limited thereto.

The latex particles having an average particle diameter within the above-described range can be prepared by adjusting the concentration of the monomer or initiator or the polymerization temperature.

First Dry Particles P1 Having Label

The type of the label of the first dry particles P1 is not particularly limited as long as it is detectable by the SPF method. The label is preferably a fluorescent substance. The first dry particles P1 having a label are preferably fluorescent latex particles. In a case in which fluorescent latex particles are used as the first dry particles P1 having a label, when the latex obtained by polymerization is fluorescent, the latex can be directly used as fluorescent latex particles. When the latex obtained by polymerization is non-fluorescent, fluorescent latex particles can be prepared by adding a fluorescent substance (fluorescent dye or the like) to the latex. That is, the fluorescent latex particles can be prepared by adding a fluorescent dye to a latex particle solution containing water and a water-soluble organic solvent and by then stirring the mixture. The latex concentration in the latex particle solution is preferably 0.1% by mass to 10% by mass. The solution preferably contains an electrolyte. As the electrolyte, NaCl is preferable, and the electrolyte concentration in the solution is preferably 1 mM to 500 mM. In addition, as the water-soluble organic solvent contained in the latex particle solution, tetrahydrofuran (THF), dimethylformamide (DMF), dimethylacetamide (DMAc), or acetone is preferable. The proportion of the water and the water-soluble organic solvent is preferably approximately 10% by mass to 80% by mass.

As described above, the expression "fluorescent latex particles" described in this specification includes both fluorescent latex particles obtained when the latex obtained by polymerization is fluorescent, and fluorescent latex particles obtained by adding a fluorescent substance (fluorescent dye or the like) to non-fluorescent latex obtained by polymerization.

Second Dry Particles P2 Having No Label

The second dry particles P2 are preferably latex particles. The latex particles can be produced by stirring a latex particle solution containing water and a water-soluble organic solvent. The latex concentration in the latex particle solution is preferably 0.1% by mass to 10% by mass. The solution preferably contains an electrolyte. As the electrolyte, NaCl is preferable, and the electrolyte concentration in the solution is preferably 1 mM to 500 mM. In addition, as the water-soluble organic solvent contained in the latex particle solution, tetrahydrofuran (THF), dimethylformamide (DMF), dimethylacetamide (DMAc), or acetone is preferable. The proportion of the water and the water-soluble organic solvent is preferably approximately 10% by mass to 80% by mass.

First Binding Substance M1

Preferable examples of the first binding substance M1 include antigens, antibodies, and complexes thereof, but are not limited thereto. For example, when the first binding substance M1 is an antibody, for example, antiserum prepared from the serum of an animal immunized with the test substance, an immunoglobulin fraction purified from antiserum, a monoclonal antibody obtained by cell fusion using splenocytes of an animal immunized with the test substance or fragments thereof (for example, F(ab')2, Fab, Fab', or Fv), and the like can be used as an antibody having specific bindability to the test substance. These antibodies can be prepared using conventional methods. Moreover, these antibodies may be modified antibodies such as chimeric antibodies, and it is also possible to use both commercially available antibodies and antibodies prepared from animal serum or culture supernatant using known methods. When the first binding substance M1 is an antibody, in regard to an epitope of the test substance to be recognized, an antibody which recognizes an epitope different from an epitope of the test substance to be recognized when the third binding substance M3 is an antibody is preferably used.

The antibodies can be used regardless of the type of animal, the subclass thereof, and the like. For example, the antibodies which can be used in the invention include antibodies derived from living organisms such as mice, rats, hamsters, goats, rabbits, sheep, cows, or chickens in which an immune reaction may occur. Specific examples thereof include mouse IgG mouse IgM, rat IgG rat IgM, hamster IgG hamster IgM, rabbit IgG rabbit IgM, goat IgG goat IgM, sheep IgG sheep IgM, cow IgG cow IgM, and chicken IgY, and both polyclonal and monoclonal antibodies can be used. Fragmented antibodies are molecules which have at least one antigen-binding site and are derived from complete antibodies, and specific examples thereof include Fab and F(ab')2. These fragmented antibodies are molecules obtained through an enzymatic or chemical process or using a genetic engineering method.

The method of immobilizing a binding substance such as an antibody or an antigen onto particles is described in, for example, JP2000-206115A, the protocol attached to Fluo-Spheres (registered trade mark) polystyrene microspheres F8813 (Molecular Probes), and the like, and any of known methods of preparing a reagent for an immunoagglutination reaction can be used. As the principle of immobilizing an antibody as a binding substance onto particles, any of principles of physical adsorption and chemical binding established by covalent bonds can be employed. As a blocking agent covering the particle surface which has not been covered with the antibody after the immobilization of the antibody onto the particles, known substances, e.g., bovine serum albumin (BSA), skim milk, casein, soybean-derived components, fish-derived components, polyethylene glycol, and commercially available blocking agents for an immune reaction containing the above substances or substances having the same properties as those of the above substances can be used. If necessary, these blocking agents can be subjected to a pretreatment such as partial denaturation by means of heat, an acid, an alkali, and the like.

Second Binding Substance M2

The second binding substance M2 is not particularly limited as long as it is, for example, a binding substance (antibody) or a compound having neither specific bindability to the test substance nor affinity for the third binding substance M3 and the first binding substance M1, such as proteins (Protein A and Protein G) binding to the binding substance (antibody), and any compound can be preferably used. For example, when the second binding substance M2 is an antibody, an immunoglobulin fraction purified from antiserum prepared from the serum of an animal immunized with the test substance, a monoclonal antibody obtained by cell fusion using splenocytes of an animal immunized with the test substance or fragments thereof (for example, F(ab')2, Fab, Fab', or Fv), and the like can be used. These antibodies can be prepared using conventional methods. Moreover, these antibodies may be modified antibodies such as chimeric antibodies, and it is also possible to use both commercially available antibodies and antibodies prepared from animal serum or culture supernatant using known methods. When the second binding substance M2 is an antibody, in regard to an epitope of the test substance to be recognized, an antibody which recognizes an epitope different from an epitope of the test substance to be recognized when the third binding substance M3 is an antibody is preferably used.

The test substance measurement kit 10 configured as described above is set in the test substance measurement device 50 to measure the amount of a test substance through the following method.

A solution in which a test sample (or extract thereof) which may contain a test substance, first dry particles P1, and second dry particles P2 are mixed and dissolved is prepared. This solution is poured from the inflow port 21 and moved in the channel by sucking the air in the channel from the discharge port 22 so that the solution is brought into contact with the first metal film 11 and the second metal film 12 in order. Thereafter, the substrate 1 may be washed in order to remove the first dry particles P1 and the second dry particles P2 which do not bind on the first metal film 11 and the second metal film 12 on the substrate 1. Next, a first signal intensity from the first dry particles P1 binding to the first metal film 11 is detected and a second signal intensity from the first dry particles P1 binding to the second metal film 12 is detected to correct the first signal intensity with the second signal intensity, and thus the concentration of the test substance is accurately measured.

The example in which a sandwich method is used as the method of measuring the concentration of the test substance has been described, but a competition method can also be employed. When the competition method is employed, the test substance measurement kit 10 has a configuration in which the substance fixed to the first metal film 11 is changed to a fifth binding substance having bindability to the first binding substance M1.

As the fifth binding substance, the test substance is used as is, or a compound having a site similar to the test substance and having an epitope with respect to the first binding substance M1 similarly to the test substance is used. Hereinafter, a measurement method based on the competition method will be described.

A solution in which a test sample (or extract thereof) which may contain a test substance, first dry particles P1, and second dry particles P2 are mixed and dissolved is prepared. This solution is poured from the inflow port 21 and moved in the channel by sucking the air in the channel from the discharge port 22 so that the solution is brought into contact with the first metal film 11 and the second metal film 12 in order.

When no test substance exists in the test sample, the fifth binding substance fixed to the first metal film 11 binds to the first binding substance M1 modifying the first dry particles P1, and the first dry particles P1 adhere to the first metal film 11 due to the contact. When the test substance exists in the test sample, the first binding substance M1 modifying the first dry particles P1 binds to the test substance at the time of the solution preparation, and thus the binding between the fifth binding substance fixed to the first metal film 11 and the test substance is inhibited. That is, the first dry particles P1 do not adhere to the first metal film 11.

In any of the case in which the test substance exists in the test sample and the case in which the test substance does not exist in the test sample, when the solution after passing the first metal film 11 is brought into contact with the second metal film 12, an action similar to that of the sandwich method occurs in the second metal film 12, and the first dry particles P1 and the second dry particles P2 adhere to each other in the second metal film 12. Since a large difference is also generated in the number of adhering particles between the first metal film 11 and the second metal film 12 in the competition method, making the second metal film 12 thinner than the first metal film 11 is effective.

In the competition method, a plurality of test samples which have different test substance concentrations and of which the amount of the test substance is known are prepared in advance. While the plurality of test samples and the first dry particles P1 are brought into contact with the measurement region, fluorescence signals from the measurement region are measured at plural different times. From the plurality of measurement results, a temporal change (slope) in the amount of fluorescence at each test substance concentration is obtained. A graph in which the Y-axis indicates the temporal change and the X-axis indicates the test substance concentration is plotted, and an appropriate fitting method such as a method of least squares is used, whereby a calibration curve of the test substance concentration relative to the temporal change in the amount of fluorescence is obtained. Based on the calibration curve obtained in this manner, it is possible to determine, from the result of the temporal change in the amount of fluorescence obtained using a target test sample, the amount of the test substance contained in the test sample.

In the above description, the fourth binding substance fixed to the second metal film 12 of the test substance measurement kit 10 has bindability to each of the first binding substance M1 and the second binding substance M2, but may have bindability only to the first binding substance M1. As described above, since the proportion of the test substance in the solution supplied to the channel is small, the number of particles adhering to the second metal film 12 is larger than the number of particles adhering to the first metal film 11 even when the second binding substance M2 does not adhere to the second metal film. Accordingly, setting a difference in the thickness between the first metal film 11 and the second metal film 12 is effective.

In addition, in the above description, the second dry particles P2 have been described to have no label, but may have a label. In this configuration, the number of particles adhering to the second metal film 12 is also larger than the number of particles adhering to the first metal film 11, and thus setting a difference in the thickness between the first metal film 11 and the second metal film 12 is effective.

According to the test substance measurement kit 10 and the test substance measurement method using the test substance measurement kit of this embodiment, even when a variation is caused in the angle of excitation light incident on the metal film, the test substance can be measured without a reduction in accuracy. Accordingly, it is not necessary to adjust the incidence angle with ultrahigh accuracy, and thus the production yield of the test substance measurement device can be improved or the production cost can be reduced. According to the test substance measurement kit 10, even when a production variation is caused in the film thickness of the metal film, the test substance can be measured without a reduction in accuracy, and thus data measurement can be accurately performed without a fluctuation in the measurement accuracy resulting from an individual difference of the kit.

Hereinafter, examples of the invention will be described.

EXAMPLES

Example 1

Preparation of Latex Particles Having Average Particle Diameter of 150 nm 30 g (288 mmol) of styrene (manufactured by Wako Pure Chemical Industries, Ltd.) and 3 g (42 mmol) of acrylic acid (manufactured by Wako Pure Chemical Industries, Ltd.) were suspended in 440 mL of ultrapure water, the resultant was heated to 95° C., and an aqueous solution obtained by dissolving 1 g of potassium persulfate (KPS) (manufactured by Wako Pure Chemical Industries, Ltd.) in 10 mL of water was added thereto, followed by stirring at 95° C. for 6 hours at 250 rpm. Thereafter, centrifugation (10,000 rpm, 6 hours) was performed to remove the supernatant liquid and redispersion in the ultrapure water was conducted. The operation from the centrifugation to the redispersion was repeated a total of three times and latex particles having a solid content concentration of 2% by mass were prepared. Pure water was added thereto to prepare a solution in which the solid content concentration of the latex particles was 1% by mass, and a median diameter (d=50) was obtained through the measurement at a temperature of 25° C. using a particle diameter analyzer FPAR-1000 (Otsuka Electronics Co., Ltd.). It was found that the latex particles have an average particle diameter of 150 nm.

Preparation of Fluorescent Latex Particles 100 mL of methanol was added to 100 mL of the aqueous dispersion of latex particles having a solid content concentration of 2% by mass prepared as described above, and the resultant was stirred for 10 minutes at room temperature. A fluorescence dye (NK136, manufactured by Hayashibara Biochemistry Laboratory) solution (obtained by dissolving the dye in a mixture of 1 mL of DMF, 9 mL of $CHCl_3$, and 16 mL of EtOH) which was separately prepared was slowly added dropwise to the latex solution in a stirring state over 60 minutes. After the dropwise addition ended, the organic solvent was distilled under reduced pressure using an evaporator, centrifugation (15,000 rpm, 15 minutes, 4° C.) was performed to remove the supernatant liquid, and redispersion was performed using a 0.01 mol/L aqueous solution of phosphate buffered saline (PBS). The operation from the centrifugation to the redispersion was repeated a total of three times and the preparation of fluorescent latex particles ended.

Preparation of Fluorescent Latex Particles Labeled with Anti-TSH Antibody

Fluorescent particles labeled with an anti-TSH antibody were prepared as described below.

250 μL of a 50 mM MES (2-morpholino ethanesulfonic acid monohydrate) buffer (pH 6.0) solution was added to 250 μL of a 2% by mass (solid content concentration) aqueous solution of fluorescent latex particles (average particle diameter of 150 nm), and 100 μL of 5 mg/mL of an anti-TSH monoclonal antibody (manufactured by Meridian Life Science, Inc.; Anti-TSH MAb MAT04-410) was added thereto, followed by stirring at room temperature for minutes. Thereafter, 5 μL of a 10 mg/mL aqueous solution of EDC (1-ethyl-3-(3-dimethylaminopropyl)carbodiimide hydrochloride, manufactured by Wako Pure Chemical Industries, Ltd.) was added to the resultant, followed by stirring at room temperature for 2 hours. 25 μL of a 2 mol/L aqueous solution of Glycine (manufactured by Wako Pure Chemical Industries, Ltd.) was added thereto, and then the resultant was stirred for 30 minutes and subjected to centrifugation (15,000 rpm, 4° C., 15 minutes) to precipitate fluorescent latex particles. Subsequently, the supernatant was removed, 500 μL of a PBS solution (pH 7.4) was added to the resultant, and the fluorescent latex particles were redispersed using an ultrasonic washing machine. Centrifugation (15,000 rpm, 4° C., 15 minutes) was performed again to remove the supernatant, and then 500 μL of a PBS solution (pH 7.4) containing 1% by mass of BSA was added to the resultant and the fluorescent latex particles were redispersed, thereby preparing a 1% by mass solution of anti-TSH antibody-bound fluorescent latex particles.

Preparation of Particles Having No Fluorescent Label

Latex particles labeled with an anti-T4 antibody were prepared as described below.

250 μL of a 50 mM IVIES buffer (pH 6.0) solution was added to 250 μL of a 2% by mass (solid content concentration) aqueous solution of latex particles (average particle diameter of 150 nm), and 100 μL of 5 mg/mL of an anti-T4 monoclonal antibody (manufactured by Medix Biochemica, Anti-Thyroxine monoclonal antibody (6901)) was added thereto, followed by stirring at room temperature for 15 minutes. Thereafter, 5 μL of a 10 mg/mL EDC aqueous solution was added to the resultant, followed by stirring at room temperature for 2 hours. 25 μL of a 2 mol/L aqueous solution of Glycine (manufactured by Wako Pure Chemical Industries, Ltd.) was added thereto, and then the resultant was stirred for 30 minutes and subjected to centrifugation (15,000 rpm, 4° C., 15 minutes) to precipitate latex particles. Subsequently, the supernatant was removed, 500 μL of a PBS solution (pH 7.4) was added to the resultant, and the latex particles were redispersed by an ultrasonic washing machine. Centrifugation (15,000 rpm, 4° C., 15 minutes) was performed again to remove the supernatant, and then 500 μL of a PBS solution (pH 7.4) containing 1% by mass of BSA was added to the resultant and the latex particles were redispersed, thereby preparing a 1% by mass solution of anti-T4 antibody-bound fluorescent latex particles.

Preparation of Fluorescent-Labeled Particles and Dry Particles Having No Fluorescent Label 280 μL of ultrapure water, 427 μL of a 12.5% by mass sucrose aqueous solution, 133 μL of a 20% by mass BSA aqueous solution, 80 μL of 1% by mass fluorescent latex particles labeled with an anti-TSH antibody (average particle diameter of 150 nm), and 320 μL of 1% by mass latex particles modified with an anti-T4 antibody (average particle diameter of 150 nm) were mixed together. A cup made of polypropylene (manufactured by Prime Polymer Co., Ltd., Prime Polypro random PP grade) as a base material was prepared, and 15 μL of the mixture was dripped thereinto. Thereafter, using a drying machine Super Dry (manufactured by Toyo Living Co., Ltd., Ultrasuper Dry 00 series), the mixture was dried until over 12 hours until the moisture content thereof became 15% or less, thereby preparing dry particles.

Preparation of Substrate

A plurality of rectangular gold films of 4 mm×5 mm were formed by sputtering on one surface of a substrate made of polymethylmethacrylate (PMMA, manufactured by Mitsubishi Rayon Co., Ltd., Acrypet VH-001) as a base material, and average film thicknesses of the gold films were respectively changed to 33 nm, 35 nm, 36 nm, 37 nm, 40 nm, and 44 nm. Based on values measured using a spectroscopic ellipsometer, a correspondence table between the values and transmissivities obtained using a spectrophotometer was prepared to obtain the film thickness value of each gold film by conversion from the correspondence table. A solution (concentration: 10 μg/mL in 150 mM NaCl) containing an anti-TSH monoclonal antibody (manufactured by Medix Biochemica, 5409) was dripped onto each gold film, and the antibody was immobilized by physical adsorption.

Substrate Washing and Blocking

Before being mounted on a channel of a sensor chip, the substrate prepared as described above was repeatedly washed three times using 300 μL of a previously prepared PBS solution (pH 7.4) containing a washing solution (0.05% by mass TWEEN 20 (polyoxyethylene (20) sorbitan monolaurate, manufactured by Wako Pure Chemical Industries, Ltd.)). After the washing ended, 300 μL of a PBS solution (pH 7.4) containing 1% by mass casein (manufactured by Thermo Scientific) was added in order to block the antibody-unadsorbed part on the gold film, and the substrate was left for 1 hour at room temperature. After the above-described washing with the washing solution, 300 μL of Immunoassay Stabilizer (manufactured by Advanced Biotechnologies, Inc.) was added as a stabilizer, the substrate was left for 30 minutes at room temperature to remove the solution, and the moisture thereof was completely removed using a drying machine.

Preparation of Sensor Chip

The prepared substrate was enclosed in a channel so as to have the configuration disclosed in the second embodiment of JP2010-190880A, thereby preparing a channel-type sensor chip.

Preparation of Test Sample

The serum of oriental beagle purchased from Kitayama Labes Co., Ltd. was used as a test sample.

Immunoassay for TSH Using Fluorescent Particles

Figure 7:
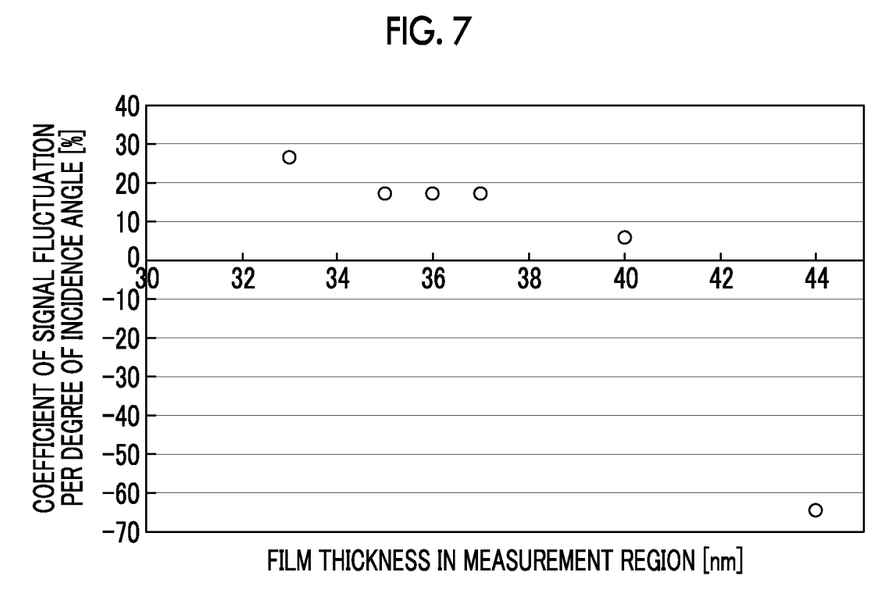
FIG. 7 is a diagram showing a measurement result of Example 1.

100 μL of the test sample (dog serum) prepared as described above was sufficiently mixed with 44 μmol of magnesium chloride. Next, this mixed sample was put into a cup containing dry fluorescent particles labeled with an anti-TSH antibody and dry latex particles labeled with an anti-T4 antibody, and mixed by stirring for 10 minutes. Next, the resultant solution was dripped onto a plurality of channel-type sensor chips in which the substrate prepared as above was enclosed. After being dripped, the mixture was allowed to flow down at a rate of 10 μL/min through suction using a pump, and the fluorescence intensity on the gold film onto which the TSH antibody had been fixed was continuously measured for 1.5 minutes. FIG. 7 shows the result of the measurement of the coefficient of fluctuation of the measurement region signal measured from the gold film with respect to the incidence angle of excitation light to the gold film.

In FIG. 7, the horizontal axis indicates the film thickness of the gold film constituting a measurement region, and the vertical axis indicates the coefficient of fluctuation of the signal detected from the measurement region when the incidence angle of the excitation light deviated from the design value by 1 deg. From the result of FIG. 7, the coefficient of fluctuation was 20% or greater when the gold film constituting the measurement region had an average film thickness of 33 nm or 44 nm. Accordingly, it was found that the coefficient of signal fluctuation per degree of the incidence angle can be reduced by adjusting the average film thickness of the gold film constituting the measurement region to 35 nm to 42 nm.

Example 2

A gold film constituting a measurement region was formed to have an average film thickness of 40 nm within the preferable range of Example 1, and gold films respectively having average film thicknesses of 16 nm, 20 nm, 24 nm, 28 nm, 32 nm, and 36 nm were formed by sputtering in the vicinity of the measurement region in the same manner as in Example 1 to prepare a plurality of substrates having a correction region formed thereon. A solution (concentration: 10 μg/mL in 150 mM NaCl) containing an anti-TSH monoclonal antibody (manufactured by Medix Biochemica, 5409) as a third binding substance was dripped onto the gold film of the measurement region, and the antibody was immobilized by physical adsorption. A solution (concentration: 10 μg/mL in 150 mM NaCl) containing an anti-mouse antibody (Anti-mouse IgG F(ab')2, product name: AffiniPure F(ab')2 Fragment Rabbit Anti-mouse IgG (H+L), manufactured by Jackson ImmunoResearch Inc.) as a fourth binding substance was dripped onto each gold film of the correction region, and the antibody was immobilized by physical adsorption. Using the substrate prepared as described above, the measurement was performed in the same manner as in Example 1 with the correction region treated as a signal detection target region.

Figure 8:
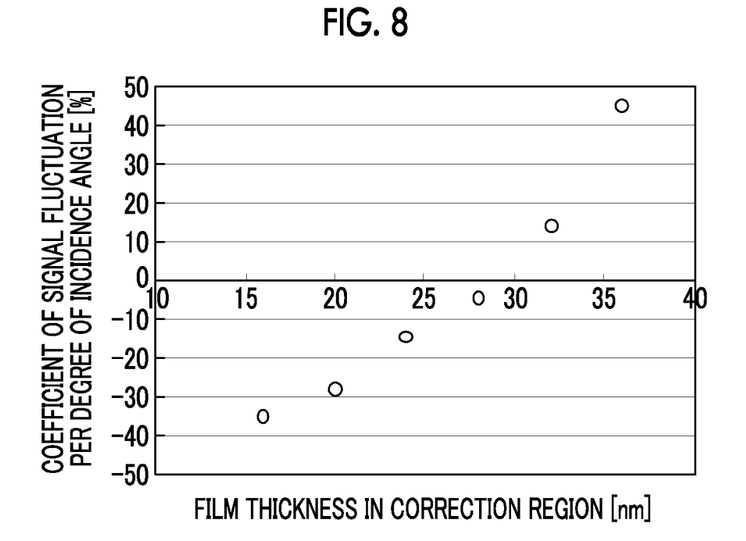
FIG. 8 is a diagram showing a measurement result of Example 2.

In FIG. 8, the horizontal axis indicates the average film thickness of the gold film constituting the correction region, and the vertical axis indicates the coefficient of fluctuation of the signal obtained by correcting the signal detected from the measurement region with the signal detected from the correction region when the incidence angle of the excitation light deviated from the design value by 1 deg.

From the result of FIG. 8, it was found that a reduction in correction accuracy resulting from the fluctuation in the incidence angle can be prevented by adjusting the average film thickness of the gold film of the correction region to 24 nm to 32 nm.

Example 3

A substrate in which the average film thickness of a gold film of a measurement region formed on the substrate was changed in the range of 32 nm to 42 nm and the average film thickness of a gold film of a correction region was changed in the range of 16 nm to 36 nm was prepared in the same manner as in Example 2. Using this substrate, signals of the measurement region and the correction region were measured in the same manner as in Example 2.

Figure 9:
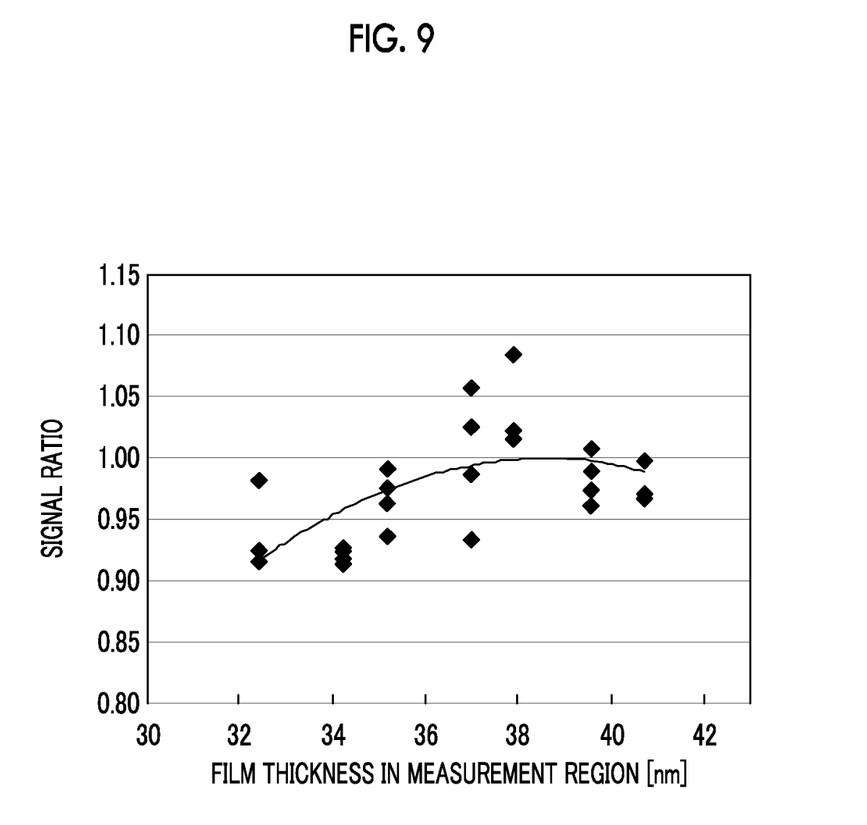
FIG. 9 is a diagram showing a measurement result of Example 3.

FIG. 9 is a diagram showing a signal ratio of the measurement region in each substrate. In FIG. 9, the signal ratio is a signal ratio of the measurement region in each substrate based on a signal of the measurement region in a substrate in which the average film thickness of the gold film of the measurement region was 37 nm.

Figure 10:
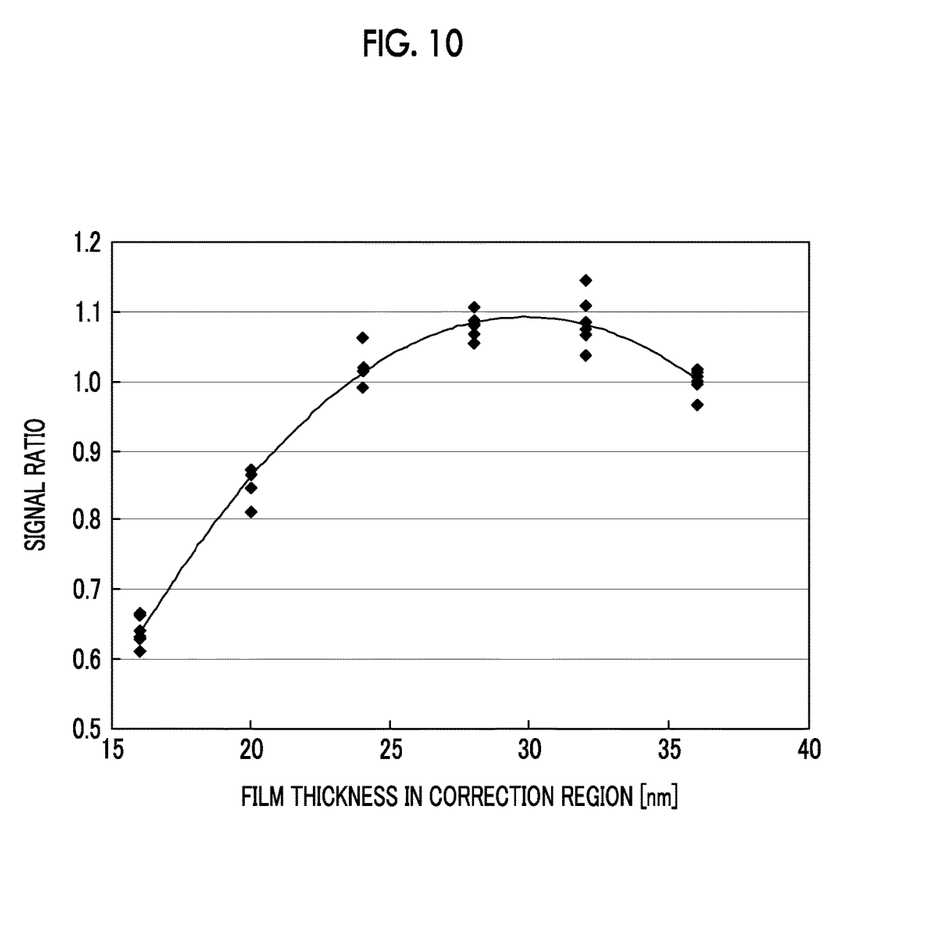
FIG. 10 is a diagram showing a measurement result of Example 3.

FIG. 10 is a diagram showing a signal ratio of the correction region in each substrate. In FIG. 10, the signal ratio is a signal ratio of the correction region in each substrate based on a signal of the correction region in a substrate in which the average film thickness of the gold film of the correction region was 36 nm.

FIGS. 9 and 10 illustrate curves obtained through a method of least squares from each plot data. From these results, it was found that the signal fluctuation is suppressed to be small when the average film thickness in the measurement region is in the range of 35 nm to 42 nm, and the average film thickness in the correction region is in the range of 24 nm to 32 nm, and thus the measurement can be performed with high accuracy even when there is a manufacturing variation in the thickness of the gold film.

As described above, this specification discloses the following items.

A test substance measurement kit disclosed includes: first dry particles which have a label and are modified with a first binding substance having specific bindability to a test substance; second dry particles which are modified with a second binding substance having no specific bindability to the test substance; and a substrate on which a first metal film to which a third binding substance having specific bindability to the test substance or a substance having bindability to the first binding substance is fixed, and a second metal film to which a fourth binding substance having no bindability to the test substance, but having bindability to the first binding substance is fixed, and which has a smaller thickness than the first metal film are formed.

In the disclosed test substance measurement kit, the second dry particles are not labeled, and the fourth binding substance has bindability to each of the first binding substance and the second binding substance.

In the disclosed test substance measurement kit, the first metal film has an average thickness of 35 nm to 42 nm, and the second metal film has an average thickness of 24 nm to 32 nm.

In the disclosed test substance measurement kit, the first dry particles have an average particle diameter of 100 nm to 200 nm, and the second dry particles have an average particle diameter of 100 nm to 200 nm.

In the disclosed test substance measurement kit, the first metal film and the second metal film contain gold.

In the disclosed test substance measurement kit, the third binding substance and the fourth binding substance are antibodies.

In the disclosed test substance measurement kit, the first dry particles are fluorescent latex particles, and the second dry particles are latex particles.

A test substance measurement method disclosed includes: bringing a solution containing a test substance, first dry particles which have a label and are modified with a first binding substance having specific bindability to the test substance, and second dry particles which are modified with a second binding substance having no specific bindability to the test substance into contact with a first metal film to which a third binding substance having specific bindability to the test substance or a substance having bindability to the first binding substance is fixed, and a second metal film to which a fourth binding substance having no bindability to the test substance, but having bindability to the first binding substance is fixed and which has a smaller thickness than the first metal film; detecting a signal according to the label from each of the first metal film and the second metal film; and correcting the signal detected from the first metal film using the signal detected from the second metal film.

In the disclosed test substance measurement method, the second dry particles are not labeled, and the fourth binding substance has bindability to each of the first binding substance and the second binding substance.

In the disclosed test substance measurement method, the first metal film has an average thickness of 35 nm to 42 nm, and the second metal film has an average thickness of 24 nm to 32 nm.

What is claimed is:

1. A test substance measurement kit comprising:
   first dry particles which have a label and are modified with a first binding substance specifically binding to a test substance;
   second dry particles which are modified with a second binding substance not specifically binding to the test substance; and
   a substrate on which a first metal film and a second metal film are formed,
   wherein the first metal film fixed to a third binding substance specifically binding to the test substance or a substance binding to the first binding substance,
   the second metal film fixed to a fourth binding substance not binding to the test substance, but binding to each of the first binding substance and the second binding substance,
   the first metal film has an average thickness of 35 nm to 42 nm, and
   the second metal film has an average thickness of 24 nm to 32 nm.

2. The test substance measurement kit according to claim 1,
   wherein the second dry particles are not labeled.

3. The test substance measurement kit according to claim 1,
   wherein the first dry particles have an average particle diameter of 100 nm to 200 nm, and
   the second dry particles have an average particle diameter of 100 nm to 200 nm.

4. The test substance measurement kit according to claim 2,
   wherein the first dry particles have an average particle diameter of 100 nm to 200 nm, and
   the second dry particles have an average particle diameter of 100 nm to 200 nm.

5. The test substance measurement kit according to claim 1,
   wherein the first metal film and the second metal film contain gold.

6. The test substance measurement kit according to claim 2,
   wherein the first metal film and the second metal film contain gold.

7. The test substance measurement kit according to claim 1,
   wherein the third binding substance and the fourth binding substance are antibodies.

8. The test substance measurement kit according to claim 2,
   wherein the third binding substance and the fourth binding substance are antibodies.

9. The test substance measurement kit according to claim 1,
   wherein the first dry particles are fluorescent latex particles, and
   the second dry particles are latex particles.

10. The test substance measurement kit according to claim 2,
    wherein the first dry particles are fluorescent latex particles, and
    the second dry particles are latex particles.

11. A test substance measurement method using the test substance measurement kit according to claim 1 comprising:
    bringing a solution containing a test substance, first dry particles which have a label and are modified with a first binding substance having specific bindability to the test substance, and second dry particles which are modified with a second binding substance having no specific bindability to the test substance into contact with a first metal film to which a third binding substance having specific bindability to the test substance or a substance having bindability to the first binding substance is fixed, and a second metal film to which a fourth binding substance having no bindability to the test substance, but having bindability to the first binding substance is fixed and which has a smaller thickness than the first metal film;
    detecting a signal according to the label from each of the first metal film and the second metal film; and
    correcting the signal detected from the first metal film using the signal detected from the second metal film.

12. The test substance measurement method according to claim 11,
    wherein the second dry particles are not labeled, and
    the fourth binding substance has bindability to each of the first binding substance and the second binding substance.

13. The test substance measurement method according to claim 11,
    wherein the first metal film has an average thickness of 35 nm to 42 nm, and
    the second metal film has an average thickness of 24 nm to 32 nm.

14. The test substance measurement method according to claim 12,
    wherein the first metal film has an average thickness of 35 nm to 42 nm, and
    the second metal film has an average thickness of 24 nm to 32 nm.

* * * * *